United States Patent [19]

Whistler

[11] 4,420,489

[45] Dec. 13, 1983

[54] SUGARS WITH SULFUR REPLACING THE RING OXYGEN ATOM AS ANTIRADIATION AGENTS

[75] Inventor: Roy L. Whistler, West Lafayette, Ind.

[73] Assignee: Purdue Research Foundation, West Lafayette, Ind.

[21] Appl. No.: 309,280

[22] Filed: Oct. 7, 1981

Related U.S. Application Data

[63] Continuation-in-part of Ser. No. 180,304, Aug. 22, 1980, abandoned.

[51] Int. Cl.$^3$ ............................................. A61K 31/38
[52] U.S. Cl. ................................................. 424/275
[58] Field of Search ....................................... 424/275

[56] References Cited

PUBLICATIONS

Meito Sango–Chem. Abst., vol. 88 (1978), pp. 65,991k and 65992m.
Song et al.–Radiology, vol. 123(1) (1977), pp. 201–205.

*Primary Examiner*—Sam Rosen
*Attorney, Agent, or Firm*—O'Rourke & Harris

[57] ABSTRACT

Simple sugars with sulfur replacing the ring oxygen atom protect normal healthy cells of animals from radiation or from any other reaction that produces free radicals and damages the cells through the action of the free radicals. To be effective, the thio-sugars must undergo transport to cells that may be adversely affected by free radicals. 6-Thio-D-fructose is an example of a sugar that is readily transported from the gastrointestinal tract to the cardiovascular system and thereby disseminated to cells throughout the body. As it is absorbed into the cells, it protects against all kinds of radiation that adversely affects cells through the creation of free radicals. It is believed to be effective against all high-energy radiation that produces free radicals in living material, and therefore is effective against radiation such as X-ray, gamma, alpha, pi mesons, neutrons, and ultraviolet light radiation. Therefore, it even offers protection against sunburn.

7 Claims, No Drawings

SUGARS WITH SULFUR REPLACING THE RING OXYGEN ATOM AS ANTIRADIATION AGENTS

This application is a continuation-in-part of my co-pending application Ser. No. 180,304, filed Aug. 22, 1980, now abandoned.

This invention relates to sugars, and particularly to sugars with sulfur replacing the ring oxygen atom to protect normal cells in animals from radiation or from any other reaction that produces free radicals and damages normal cells through the action of such free radicals.

Explorations have been conducted into the likely medical value of sugar analogs which structurally and conformationally mimic naturally occurring sugars, but by subtle differences cause the sugars to behave differently from their natural analogs. One such variance in structure, replacement of the normal ring oxygen atom of cyclic sugar with a sulfur atom, has been explored. Replacement of divalent oxygen with divalent sulfur only slightly changes the size of the sugar ring because of the slightly larger size of the sulfur. Further, the electronegative oxygen is replaced by the slightly less electronegative sulfur. Chemical means are available for synthesizing sugars with sulfur replacing the ring oxygen. See, for example, Paulsen, H. and K. Todt, "Cyclic Monosaccharides Having Nitrogen or Sulfur in the Ring," 23 *Advances in Carbohydrate Chemistry*, 116 et seq. (1968).

When 5-thio-D-glucose, the D-glucose analog with sulfur replacing the ring oxygen, was made and examined, it was found to have the same conformation as natural D-glucose. However, it was slightly sweeter than natural D-glucose and only very slowly metabolized. It was essentially non-toxic with an $LD_{50}$ of 14 g/kg. In rats, it was about 98% excreted, mostly unchanged. Its principal effect was to inhibit cellular absorption of natural D-glucose and to bring about cessation of carbohydrate metabolism. In the presence of 5-thio-D-glucose, the cells were thus required to use lipids or proteins for energy. Further, since high D-glucose levels are required in male testes for sperm development, 5-thio-D-glucose was shown to be a male anti-fertility agent. 5-Thio-D-glucose was shown to inhibit development and growth of tapeworms and trypanosomes in rats, presumably because of its effect of reducing D-glucose utilization in these parasites. It was further shown to inhibit development of neoplastic cells, and to kill neoplastic cells. Therefore, it was believed to be useful as an anti-tumor agent. It was demonstrated to be lethal against hypoxic (anaerobic) cells. It further showed powerful assistant action in killing cancer cells when aided by X-ray or other radiation treatment. It was further believed that 5-thio-D-glucose would be useful in protecting normal cells of animals from radiation or any other reaction that produces free radicals and that damages normal cells through the action of such free radicals. Although useful as an antiradiation agent, it is unlikely that 5-thio-D-glucose would be generally applied as a radiation protective agent, since the sugar analog was demonstrated to inhibit cellular absorption of natural D-glucose, inhibit carbohydrate metabolism, and promote male infertility.

An investigation of other cyclic sugars with sulfur replacing the ring oxygen atom was conducted to determine whether any other such sugars exhibited radiation protective effects without the adverse effects of 5-thio-D-glucose. According to the invention, cyclic sugars with sulfur replacing the ring oxygen atom are useful to minimize the effects of free radicals on living cells. Of course, to be useful, the thio-sugars must be capable of being transported to all cells that may be adversely affected by the free radicals. As discussed above, although not all sugars are equally effective to minimize the production of free radicals in living cells, 6-thio-D-fructose has been shown to be useful in the prevention of radiation-induced free radical production and to inhibit damage due to radiation. 6-Thio-D-fructose is ideal, since it can be given orally to an animal or human and is readily transported from the gastrointestinal tract to the cardiovascular system for delivery to cells throughout the body. Of course, 6-thio-D-fructose could be given intraperitoneally for faster action if fast action should be desirable. As 6-thio-D-fructose is transported into the cells, it protects against all kinds of radiation that adversely affect the cells through the creation of free radicals. Additional considerations which make 6-thio-D-fructose particularly useful here are that it is essentially non-toxic, with an $LD_{50}$ of 11.2 g/kg or higher. The 6-thio-D-fructose is a sweet-tasting sugar, surpassing its natural analog, D-fructose, in sweetness.

Since 6-thio-D-fructose protects directly against free radicals, it is effective against several known forms of high-energy radiation that produce free radicals in living material. It is, for example, effective against radiation such as X-ray, gamma, alpha, pi mesons, neutrons, ultraviolet light, etc., and against substances such as chemicals or drugs that can produce free radicals. For proper usage, the sulfur sugar analog is given orally about one-half to two hours before exposure to radiation. Its protective effect will persist for approximately six hours. Longer protection requires repeated doses. The quantity given can vary over a rather broad range, but normally would be in amounts of, for example, 10 mg/kg to 500 mg/kg with 50 mg/kg being ample for protection from relatively heavy radiation. Among other sulfur sugars that transport well in the body are 5-thio-D-galactose, 5-thio-2-deoxyribose, and 5-thio-D-ribose. To a lesser extent, other sulfur sugars also transport in the body. The ring size may be either five or six members (furanose or pyranose, respectively). The sugars may contain any number of carbon atoms, although pentoses and hexoses (five carbon atoms or six carbon atoms, respectively) are most readily available. The free radical suppression effect seems not to depend upon whether the sugar structure is a ketose or an aldose structure. All that is essential is that the sulfur sugar be assimilated into the body. It is believed that the ability of the ring sulfur atom to assume different valences other than the divalent form necessary to replace the ring oxygen is what permits a sulfur sugar to capture free radicals, and renders it effective as an antiradiation agent.

EXAMPLE I

A mature Wistar white rat was given 50 mg/kg of 6-thio-D-fructose by lavage (stomach tube) two hours before being subject to full body radiation with clinical X-rays in varying dosages. After 3 days and 10 days, rats treated with 6-thio-D-fructose showed considerable less effect even to less erythema than control animals that were given equivalent X-ray treatment but not given 6-thio-D-fructose.

EXAMPLE II

6-Thio-D-fructose ($LD_{50}$ 17.5 grams per kilogram) dissolved in water, was administered intraperitoneally at a dose of 500 mg per kg to 14 rats 30 minutes before they were subjected to 950 rads of X-ray whole-body radiation. This amount of X-ray radiation is the X-ray $LD_{100}$ plus 50 rads at 30 days. All 14 rats survived for 30 days.

EXAMPLE III

To determine tissue protective capabilities of 6-thio-D-fructose, it was tested with cisplatin, an alkylating agent used in treatment of testicular and ovarian tumors. Usefulness is limited by production of cumulative nephrotoxicity. In a test group of rats cisplatin was administered in increasing amounts of 5, 7.5 and 10 mg/kg interperitoneally and 500 mg of 6-thio-D-fructose separately administered intraperitoneally. The blood-urea-nitrogen (BUN) was measured to determine the protection provided. With control animals the BUN at 5 days was $70\pm12$, $198\pm32$ and death while the 6-thio-D-fructose protected animals had BUN values of $26\pm3$, $164\pm3$ and $323\pm3$ for the comparable levels of cisplatin at 5, 7.5 and 10 mg/kg respectively.

What is claimed is:

1. A method of treatment of an animal utilizing a ring sugar with sulfur replacing a ring oxygen atom, said method comprising the step of treating said animal with a sulfur sugar that does not adversely affect the cellular metabolism of the animal and which is transportable into the animal's cells prior to exposure of the animal to electromagnetic radiation, with the dosage of said sulfur sugar utilized to treat said animal being in an effective amount of minimize the effect of electromagnetic radiation-induced free radicals on the animal's cells.

2. A method of treatment of an animal utilizing a ring sugar with sulfur replacing a ring oxygen atom, said method comprising the step of treating said animal with a sulfur sugar that does not adversely affect the cellular metabolism of the animal, with said sulfur sugar having a ring size of one of 5 and 6 members and with said sulfur sugar being transportable into the animal's cells, and with the dosage of said sulfur sugar utilized to treat said animal being in an effective amount to minimize the effect of free radicals on the animal's cells.

3. A method of treatment of a living organism to minimize the effect of free radicals on the living organism's cells, said method comprising the steps of administering to the living organism a ring sugar with sulfur replacing a ring oxygen atom, said ring sugar having a ring size of one of 5 and 6 members with said ring sugar not adversely affecting the cellular metabolism of the animal and with the dosage of said sulfur sugar administered to said living organism being non-toxic and in an effective amount to minimize the effect of free radicals on the animal's cells.

4. A method of treatment of a living organism's tissue to minimize the effect of free radicals on the tissue, said method comprising the steps of determining the identity of a ring sugar that does not adversely affect the cellular metabolism of the animal and has a ring size of one of 5 and 6 members with said ring sugar having a ring oxygen atom replaced by a sulfur atom which is transportable into the cells of the tissue, and treating the tissue with that sulfur sugar with the dosage of said sulfur sugar utilized to treat said tissue being between about 10 mg/kg and 500 mg/kg.

5. A method of treating an animal to minimize the effect of introduced substances that may adversely affect the animal by free radical creation, said method comprising introduction into the system of said animal of a sugar having sulfur as the ring atom in a dosage sufficient to substantially counteract the effect of said free radical, said sulfur sugar being selected from one of the group consisting of 6-thio-D-fructose, 5-thio-D-galactose, 5-thio-2-deoxyribose, and 5-thio-D-ribose and mixtures thereof.

6. The method of claim 1, 2, 3, or 4 wherein the sulfur sugar is one selected from the group consisting of 6-thio-D-fructose, 5-thio-D-galactose, 5-thio-2-deoxyribose, and 5-thio-D-ribose and mixtures thereof.

7. A method of treatment of an animal to minimize the effect of free radicals on the animal's tissue, the treatment method comprising the steps of determining the identity of a ring sugar having a ring oxygen atom replaced by a sulfur atom which is transportable through the animal's gastrointestinal tract to the animal's cardiovascular system and is absorbed from the animal's cardiovascular system into the animal's cells, said ring sugar being selected from the group consisting of 6-thio-D-fructose, 5-thio-D-galactose, 5-thio-2-deoxyribose, and 5-thio-D-ribose and mixtures thereof, and causing the animal to ingest said ring sugar in a dosage of between about 10 mg/kg and 500 mg/kg.

* * * * *